(12) United States Patent
ShafieiBavani et al.

(10) Patent No.: US 11,694,113 B2
(45) Date of Patent: Jul. 4, 2023

(54) PERSONALIZED AND ADAPTIVE LEARNING AUDIO FILTERING

(71) Applicant: INTERNATIONAL BUSINESS MACHINES CORPORATION, Armonk, NY (US)

(72) Inventors: Elaheh ShafieiBavani, Melbourne (AU); Fatemeh Jalali, Hawthorn East (AU); Mahtab Mirmomeni, Hawthorne East (AU); Ying Xu, Albion (AU)

(73) Assignee: International Business Machines Corporation, Armonk, NY (US)

( * ) Notice: Subject to any disclaimer, the term of this patent is extended or adjusted under 35 U.S.C. 154(b) by 580 days.

(21) Appl. No.: 16/809,648

(22) Filed: Mar. 5, 2020

(65) Prior Publication Data
US 2021/0279634 A1 Sep. 9, 2021

(51) Int. Cl.
*G06N 20/00* (2019.01)
*G10L 25/57* (2013.01)
(Continued)

(52) U.S. Cl.
CPC ............ *G06N 20/00* (2019.01); *G06F 3/015* (2013.01); *G06V 20/46* (2022.01); *G10L 25/57* (2013.01)

(58) Field of Classification Search
CPC ........ G06N 20/00; G06V 20/46; G06F 3/015; G10L 25/57
See application file for complete search history.

(56) References Cited

U.S. PATENT DOCUMENTS 5,825,897 A  10/1998  Andrea et al.
7,698,133 B2  4/2010  Ichikawa
(Continued)

FOREIGN PATENT DOCUMENTS

WO  USPCT 2019/025931  * 4/2019 ............... G06F 3/01

OTHER PUBLICATIONS

Kickstarter, [online]; [retrieved on Feb. 28, 2020]; retrieved from the Internet, https://www.kickstarter.com/projects/dopplerlabs/here-active-listening-change-the-way-yo, 19p.
(Continued)

*Primary Examiner* — Mishawn N. Hunter
(74) *Attorney, Agent, or Firm* — Cantor Colburn LLP; Michael A. Petrocelli (57) ABSTRACT

Aspects of the invention include a method including collecting, by a processor, physiological data from a user in an environment and a sound waveform from the user's environment. The method detects and labels as a potential annoyance, by the processor, a set of potential annoyance data based on the collected physiological data and the sound waveform. The method decomposes, by the processor, the sound waveform into a first sound waveform segment associated with the set of potential annoyance data and a second sound waveform segment not associated with the set of potential annoyance data. The method predicts, by the processor, that the potential annoyance is an actual annoyance. The method filters and modifies, by the processor, the first sound waveform segment associated with the actual annoyance and provides, by the processor, the second sound waveform segment not associated with the actual annoyance to the user.

20 Claims, 3 Drawing Sheets

(51) Int. Cl.
*G06F 3/01* (2006.01)
*G06V 20/40* (2022.01)

(56) References Cited

U.S. PATENT DOCUMENTS

| | | | |
|---|---|---|---|
| 10,045,115 | B2 | 8/2018 | Klimanis et al. |
| 2014/0107521 | A1 | 4/2014 | Galan |
| 2014/0307878 | A1* | 10/2014 | Osborne ................ G16H 50/20 381/56 |
| 2015/0099946 | A1 | 4/2015 | Sahin et al. |
| 2015/0348530 | A1 | 12/2015 | Findlay et al. |
| 2016/0234595 | A1 | 8/2016 | Goran et al. |
| 2017/0142512 | A1 | 5/2017 | Klimanis et al. |
| 2018/0344968 | A1 | 12/2018 | Gordon et al. |
| 2019/0130337 | A1* | 5/2019 | Nafus .................. H04L 67/12 |
| 2019/0196777 | A1* | 6/2019 | Kovacevic ............... H04R 5/04 |

OTHER PUBLICATIONS

Morris, "Managing Sound Sensitivity in Autism Spectrum Disorder: New Technologies for Customized Intervention", Massachusetts Institute of Technology 2009, 86p.

National Austism Resources, [online]; [retrieved onFeb. 28, 2020]; retrieved from the Internet, https://www.nationalautismresources.com/headphones/, 3p.

Nuraphone, [online]; [retrieved onFeb. 28, 2020]; retrieved from the Internet, https://www.nuraphone.com/, 9p.

Osborne, "It's About Time: Synthwatch, the Synth You Can Wear on Your Wrist", https://enmoreaudio.com, Dec. 3, 2018. 7p.

Schmidt et al. "Single-channel speech separation using sparse non-negative matrix factorization." Interspeech 2006—ICSLP. vol 2. 2006. 4 pages.

Somerville et al. "Sound source separation algorithm comparison using popular music." International Conference on Music Communication Science. 2009. 5 pages.

* cited by examiner

PERSONALIZED AND ADAPTIVE LEARNING AUDIO FILTERING

BACKGROUND

The present invention generally relates to audio signal processing systems, and more specifically, to computer-implemented methods, computing systems, and computer program products configured and arranged to implement a personalized and adaptive learning audio filtering system that identifies and removes sounds that are dynamically determined to be unpleasant to a user.

Audio signal processing is a subfield of signal processing that is concerned with the electronic manipulation of audio signals. Audio signals are electronic representations of sound waves, i.e., longitudinal waves that travel through air and are formed from compressions and rarefactions. The energy contained in audio signals is typically measured in decibels. A digital representation expresses the audio waveform as a sequence of symbols, usually binary numbers. This permits signal processing using digital circuits such as digital signal processors, microprocessors and general-purpose computers.

There are a variety of audio signal processing techniques for eliminating unwanted sounds from an audio waveform. In a known approach, a signal is created that is identical to the unwanted audio signal but with the opposite polarity, and the two signals cancel each other out due to destructive interference.

SUMMARY

Embodiments of the present invention are directed to an adaptive learning sound filtering system. A non-limiting example computer-implemented method includes collecting, by a processor, physiological data from a user and a sound waveform from the user's environment. The method detects and labels as a potential annoyance, by the processor, a set of potential annoyance data based on the collected physiological data and the sound waveform. The method decomposes, by the processor, the sound waveform into a first sound waveform segment associated with the set of potential annoyance data and a second sound waveform segment not associated with the set of potential annoyance data. The method predicts, by the processor, that the set of potential annoyance data is an actual annoyance. The method filters and modifies, by the processor, the first sound waveform segment associated with the actual annoyance and provides, by the processor, the second sound waveform segment not associated with the actual annoyance to the user.

Other embodiments of the present invention implement features of the above-described method in computer systems and computer program products.

Additional technical features and benefits are realized through the techniques of the present invention. Embodiments and aspects of the invention are described in detail herein and are considered a part of the claimed subject matter. For a better understanding, refer to the detailed description and to the drawings.

BRIEF DESCRIPTION OF THE DRAWINGS

The specifics of the exclusive rights described herein are particularly pointed out and distinctly claimed in the claims at the conclusion of the specification. The foregoing and other features and advantages of the embodiments of the invention are apparent from the following detailed description taken in conjunction with the accompanying drawings in which:

The diagrams depicted herein are illustrative. There can be many variations to the diagrams or the operations described therein without departing from the spirit of the invention. For instance, the actions can be performed in a differing order or actions can be added, deleted or modified. Also, the term "coupled" and variations thereof describes having a communications path between two elements and does not imply a direct connection between the elements with no intervening elements/connections between them. All of these variations are considered a part of the specification.

DETAILED DESCRIPTION

One or more embodiments of the invention provide a computer-implemented, personalized, and adaptive learning audio filtering system. The system can be used by any person, but is particularly useful to a sound-sensitive individual suffering from any condition that makes the person sensitive to certain sound frequencies. One example of a sound-sensitive individual is an individual suffering from autism spectrum disorder (ASD).

For each individual, and particularity for sound sensitive individuals, there are sound frequencies that cause the individual to experience negative or unpleasant feelings. Children who experience sound as an unpleasant sensation, or even as physical pain, develop defensive reactions (such as covering their ears) and avoidant reactions (seeking only activities and places without excessive sound). Sound sensitive individuals, including individual suffering from ASD, frequently mention a dislike of percussive sounds; changing or unexpected sounds; and specific, intense frequencies, such as strip-lighting or the hum from computer fans and fridges. However, a sound frequency that is unpleasant to one person may or may not be unpleasant to another person. Embodiments of the invention address this issue by providing an adaptive module that adaptively changes its sound (cancelling/filtering/modifying) operations based on the sound sensitive individual's overall condition and response to a sound. In embodiments of the invention, user information is gathered from a variety of sources, including, for example, biological sensors and static information such as health records. The user information is applied to a multi-module system that uses it to adaptively update the cancelling/filtering/modifying actions of the system using machine learning methods.

Embodiments of the present invention provide a personalized and adaptive learning sound filtering system that collects real-time feedback on stress monitoring and physiological changes (i.e., changes in blood pressure, brain waves, gestures, and body language) in different environmental situations. In embodiments of the invention, the system continuously learns based on this information and provides sound filtering and/or modification that targets sounds that user feedback of the system has identified as being unpleasant to the user.

Figure 1:
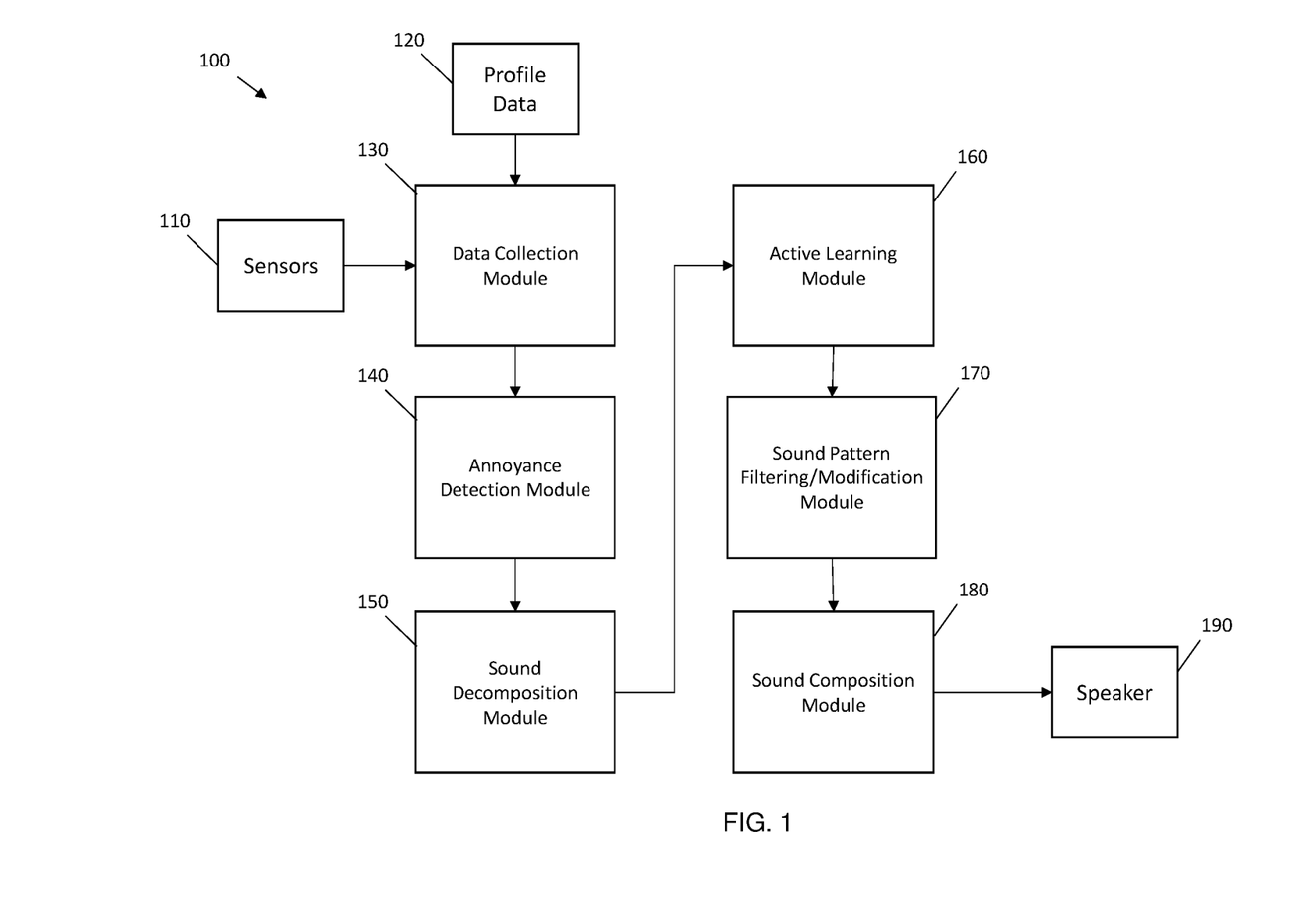
FIG. 1 illustrates a block diagram of components of an adaptive learning sound filtering system in accordance with one or more embodiments of the present invention.

Turning now to FIG. 1, a personalized and adaptive learning sound filtering system 100 is generally shown in accordance with one or more embodiments of the present invention. The modules 130, 140, 150, 160, 170, 180 of the adaptive learning sound filtering system 100 are implemented in a computer system such as computer system 300 (shown in FIG. 3). In embodiments of the invention, the computer system 300 includes a variety of machine learning algorithms configured to execute the system functionality described herein. More specifically, the computer system 300 includes trainable machine learning algorithms that extract features from training data to build a model of the user. Specifically, the machine learning algorithms are trained, using training data, to generate a model of the sound sensitivities of the user. The inputs from the sensors 110 and the profile data 120 are used to classify frequencies in a received audio waveform as an unpleasant sound that should be filtered, or as "not" an unpleasant sound, which can be passed to the user.

Sensors 110 collect physiological data using wearable sensors to indicate user reactions to surrounding sounds and collect raw sound waveforms around the user in real time. Physiological data such as brain waves, eye movement, eye contact/gaze, hear beat, blood pressure, body gestures, and stress levels are collected by sensors 110. Profile data 120 about the user is also collected. Profile data includes age, gender, job title, and medical history, for example. A data collection module 130 captures this information. The data collection module 130 also collects an environmental video feed where available.

The profile data and physiological data, including the raw sound waveforms, are received by an annoyance detection module 140. The annoyance detection module 140 records a time series of each of the physiological data streams received from the data collection module 130. The annoyance detection module 140 finds patterns of abnormal changes in this input data, for example, changes in heart rate or brain waves or annoyance behavior that may be demonstrated in the environmental video feed. The patterns are found using discovery/anomaly detection techniques using pattern recognition algorithms. The annoyance detection module 140 flags a start time and an end time of detected annoyances that form an annoyance period and labels the associated raw sound waveform's time series segment as a potential annoyance (or a non-annoyance if not applicable).

The sound decomposition module 150 receives from the annoyance detection module 140 the raw sound waveform's time series segment corresponding to the annoyance period of the potential annoyance that is to be extracted. The sound waveform segment is the segment of sound from the raw sound waveform associated with the detected, potential annoyance. The sound decomposition module 150 decomposes the sound waveform segment during the potential annoyance period into a set of different sound waveforms. A known non-negative matrix factor 2-D deconvolution algorithm can be used as the sound separation algorithm for decomposing the sound waveform segment.

An active learning module 160 is composed of a machine learning model that remains active throughout the user's use of the adaptive learning sound filtering system 100. It takes each of the decomposed sound waveforms as an input from the sound decomposition module 150 and predicts whether the decomposed sound waveforms are causing actual annoyance. Training data is composed of pairs of inputs and outputs indicated the decomposed sound waveforms and their corresponding potential annoyance/non-annoyance labels that are labeled by the annoyance detection module.

Once the model is learned, the model can predict whether a decomposed sound waveform is causing an annoyance reaction or actual annoyance, even without physiological input, user profile data, or the environmental video feed. Once predicted, the decomposed input sound waveform is labeled as an actual annoyance pattern. As different users react differently to different sounds, the machine learning model is individualized over a period of time. Also, an annoyance sound can change over time for the same user; therefore, the active learning module captures the inputs in real-time and updates the machine learning model periodically.

A sound pattern filtering module 170 receives the decomposed input sound waveforms and identifies the actual annoyance patterns identified by the active learning module 160. When an actual annoyance pattern has been detected by the active learning module 160, the sound waveform associated with the actual annoyance pattern is segmented and removed from the waveform. A sound composition module 180 receives an output of the sound pattern filtering module 170 and is used to compose the various sound waveforms back into a single waveform which is passed to a speaker 190.

Figure 2:
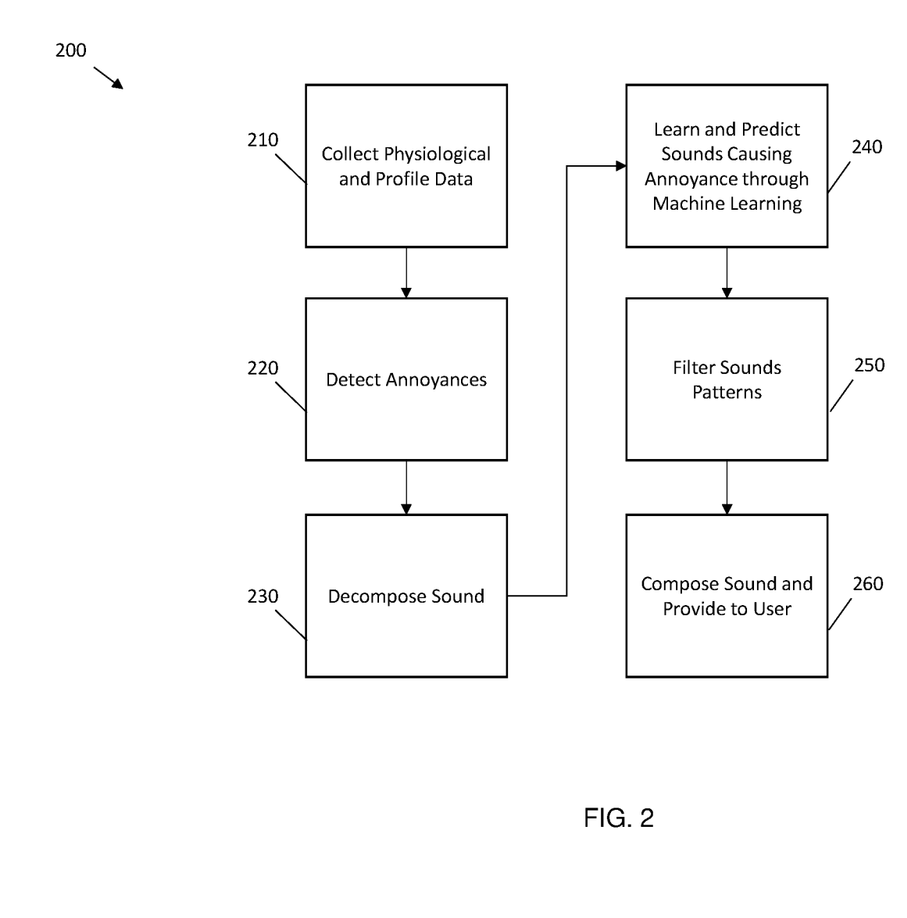
FIG. 2 illustrates a flow diagram of a process for the adaptive learning sound filtering system in accordance with one or more embodiments of the present invention.

FIG. 2 illustrates a flow diagram of a process 200 implemented by the personalized and adaptive learning sound filtering system 100 (shown in FIG. 1) in accordance with one or more embodiments of the present invention. Physiological and profile data, as well as an environment mental video feed in some embodiments of the invention, are collected by sensors and the data collection module 130. (Block 210). Potential annoyances are detected by the annoyance detection module 140 from the data collected by the data collection module 130. (Block 220). As previously discussed, patterns of abnormal changes in input data are found using discovery/anomaly detection techniques using pattern recognition algorithms.

The sound waveform segments are decomposed by the sound decomposition module during the potential annoyance period into a set of different sound waveforms. (Block 230). A non-negative matrix factor 2-D deconvolution algorithm serves as the sound separation algorithm for decomposing the sound waveform segment. A prediction is made of sounds that cause actual annoyance through a machine learning algorithm by the active learning module 160. (Block 240). The active learning model can predict whether a decomposed sound waveform is causing an actual annoyance reaction. Once predicted, the decomposed input sound waveform is labeled as an actual annoyance pattern.

Sound patterns are filtered and modified by the sound pattern filtering module 170 that receives the decomposed input sound waveforms and identifies the actual annoyance patterns identified by the active learning module 160. (Block 250). When an actual annoyance pattern has been detected by the active learning module 160, the sound waveform associated with the actual annoyance pattern is segmented and removed from the waveform. The sound is composed and provided to the user by sound composition module 180 and speaker 190.

Figure 3:
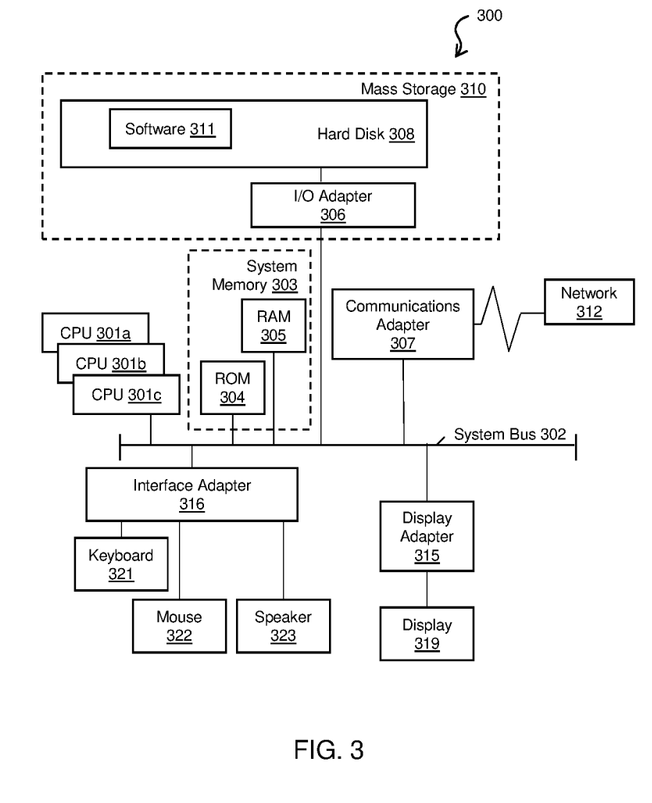
FIG. 3 depicts a computer system capable of implementing aspects of the present invention.

Turning now to FIG. 3, the computer system 300 is generally shown in accordance with embodiments of the invention. The computer system 300 can be an electronic, computer framework comprising and/or employing any number and combination of computing devices and networks utilizing various communication technologies, as described herein. The computer system 300 can be easily scalable, extensible, and modular, with the ability to change to different services or reconfigure some features independently of others. The computer system 300 may be, for example, a server, desktop computer, laptop computer, tablet computer, or smartphone. In some examples, computer system 300 may be a cloud computing node. Computer system 300 may be described in the general context of computer system executable instructions, such as program modules, being executed by a computer system. Generally, program modules may include routines, programs, objects, components, logic, data structures, and so on that perform particular tasks or implement particular abstract data types. Computer system 300 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 3, the computer system 300 has one or more central processing units (CPU(s)) 301a, 301b, 301c, etc. (collectively or generically referred to as processor(s) 301). The processors 301 can be a single-core processor, multi-core processor, computing cluster, or any number of other configurations. The processors 301, also referred to as processing circuits, are coupled via a system bus 302 to a system memory 303 and various other components. The system memory 303 can include a read only memory (ROM) 304 and a random access memory (RAM) 305. The ROM 304 is coupled to the system bus 302 and may include a basic input/output system (BIOS), which controls certain basic functions of the computer system 300. The RAM is read-write memory coupled to the system bus 302 for use by the processors 301. The system memory 303 provides temporary memory space for operations of said instructions during operation. The system memory 303 can include random access memory (RAM), read only memory, flash memory, or any other suitable memory systems.

The computer system 300 comprises an input/output (I/O) adapter 306 and a communications adapter 307 coupled to the system bus 302. The I/O adapter 306 may be a small computer system interface (SCSI) adapter that communicates with a hard disk 308 and/or any other similar component. The I/O adapter 306 and the hard disk 308 are collectively referred to herein as a mass storage 310.

Software 311 for execution on the computer system 300 may be stored in the mass storage 310. The mass storage 310 is an example of a tangible storage medium readable by the processors 301, where the software 311 is stored as instructions for execution by the processors 301 to cause the computer system 300 to operate, such as is described herein below with respect to the various Figures. Examples of computer program product and the execution of such instruction is discussed herein in more detail. The communications adapter 307 interconnects the system bus 302 with a network 312, which may be an outside network, enabling the computer system 300 to communicate with other such systems. In one embodiment, a portion of the system memory 303 and the mass storage 310 collectively store an operating system, which may be any appropriate operating system, such as the z/OS or AIX operating system from IBM Corporation, to coordinate the functions of the various components shown in FIG. 3.

Additional input/output devices are shown as connected to the system bus 302 via a display adapter 319 and an interface adapter 316 and. In one embodiment, the adapters 306, 307, 315, and 316 may be connected to one or more I/O buses that are connected to the system bus 302 via an intermediate bus bridge (not shown). A display 319 (e.g., a screen or a display monitor) is connected to the system bus 302 by a display adapter 315, which may include a graphics controller to improve the performance of graphics intensive applications and a video controller. A keyboard 321, a mouse 322, a speaker 323, etc. can be interconnected to the system bus 302 via the interface adapter 316, which may include, for example, a Super I/O chip integrating multiple device adapters into a single integrated circuit. Suitable I/O buses for connecting peripheral devices such as hard disk controllers, network adapters, and graphics adapters typically include common protocols, such as the Peripheral Component Interconnect (PCI). Thus, as configured in FIG. 3, the computer system 300 includes processing capability in the form of the processors 301, and, storage capability including the system memory 303 and the mass storage 310, input means such as the keyboard 321 and the mouse 322, and output capability including the speaker 323 and the display 319.

In some embodiments, the communications adapter 307 can transmit data using any suitable interface or protocol, such as the internet small computer system interface, among others. The network 312 may be a cellular network, a radio network, a wide area network (WAN), a local area network (LAN), or the Internet, among others. An external computing device may connect to the computer system 300 through the network 312. In some examples, an external computing device may be an external webserver or a cloud computing node.

It is to be understood that the block diagram of FIG. 3 is not intended to indicate that the computer system 300 is to include all of the components shown in FIG. 3. Rather, the computer system 300 can include any appropriate fewer or additional components not illustrated in FIG. 3 (e.g., additional memory components, embedded controllers, modules, additional network interfaces, etc.). Further, the embodiments described herein with respect to computer system 300 may be implemented with any appropriate logic, wherein the logic, as referred to herein, can include any suitable hardware (e.g., a processor, an embedded controller, or an application specific integrated circuit, among others), software (e.g., an application, among others), firmware, or any suitable combination of hardware, software, and firmware, in various embodiments.

Various embodiments of the invention are described herein with reference to the related drawings. Alternative embodiments of the invention can be devised without departing from the scope of this invention. Various connections and positional relationships (e.g., over, below, adjacent, etc.) are set forth between elements in the following description and in the drawings. These connections and/or positional relationships, unless specified otherwise, can be direct or indirect, and the present invention is not intended to be limiting in this respect. Accordingly, a coupling of entities can refer to either a direct or an indirect coupling, and a positional relationship between entities can be a direct or indirect positional relationship. Moreover, the various tasks and process steps described herein can be incorporated into a more comprehensive procedure or process having additional steps or functionality not described in detail herein.

One or more of the methods described herein can be implemented with any or a combination of the following technologies, which are each well known in the art: a discrete logic circuit(s) having logic gates for implementing logic functions upon data signals, an application specific integrated circuit (ASIC) having appropriate combinational logic gates, a programmable gate array(s) (PGA), a field programmable gate array (FPGA), etc For the sake of brevity, conventional techniques related to making and using aspects of the invention may or may not be described in detail herein. In particular, various aspects of computing systems and specific computer programs to implement the various technical features described herein are well known. Accordingly, in the interest of brevity, many conventional implementation details are only mentioned briefly herein or are omitted entirely without providing the well-known system and/or process details.

In some embodiments, various functions or acts can take place at a given location and/or in connection with the operation of one or more apparatuses or systems. In some embodiments, a portion of a given function or act can be performed at a first device or location, and the remainder of the function or act can be performed at one or more additional devices or locations.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, element components, and/or groups thereof.

The corresponding structures, materials, acts, and equivalents of all means or step plus function elements in the claims below are intended to include any structure, material, or act for performing the function in combination with other claimed elements as specifically claimed. The present disclosure has been presented for purposes of illustration and description, but is not intended to be exhaustive or limited to the form disclosed. Many modifications and variations will be apparent to those of ordinary skill in the art without departing from the scope and spirit of the disclosure. The embodiments were chosen and described in order to best explain the principles of the disclosure and the practical application, and to enable others of ordinary skill in the art to understand the disclosure for various embodiments with various modifications as are suited to the particular use contemplated.

The diagrams depicted herein are illustrative. There can be many variations to the diagram or the steps (or operations) described therein without departing from the spirit of the disclosure. For instance, the actions can be performed in a differing order or actions can be added, deleted or modified. Also, the term "coupled" describes having a signal path between two elements and does not imply a direct connection between the elements with no intervening elements/connections therebetween. All of these variations are considered a part of the present disclosure.

The following definitions and abbreviations are to be used for the interpretation of the claims and the specification. As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but can include other elements not expressly listed or inherent to such composition, mixture, process, method, article, or apparatus.

Additionally, the term "exemplary" is used herein to mean "serving as an example, instance or illustration." Any embodiment or design described herein as "exemplary" is not necessarily to be construed as preferred or advantageous over other embodiments or designs. The terms "at least one" and "one or more" are understood to include any integer number greater than or equal to one, i.e. one, two, three, four, etc. The terms "a plurality" are understood to include any integer number greater than or equal to two, i.e. two, three, four, five, etc. The term "connection" can include both an indirect "connection" and a direct "connection."

The terms "about," "substantially," "approximately," and variations thereof, are intended to include the degree of error associated with measurement of the particular quantity based upon the equipment available at the time of filing the application. For example, "about" can include a range of ±8% or 5%, or 2% of a given value.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instruction by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments described herein.

What is claimed is:

1. A computer-implemented method comprising:
   collecting, by a processor, physiological data from a user in an environment and a sound waveform from the user's environment;
   detecting and labeling as a potential annoyance, by the processor, a set of potential annoyance data based on the collected physiological data and the sound waveform;
   decomposing, by the processor, the sound waveform into a first sound waveform segment associated with the set of potential annoyance data and a second sound waveform segment not associated with the set of potential annoyance data;
   predicting, by the processor, that the set of potential annoyance data is an actual annoyance;
   filtering and modifying, by the processor, the first sound waveform segment associated with the actual annoyance; and
   providing, by the processor, the second sound waveform segment not associated with the actual annoyance to the user.

2. The computer-implemented method of claim 1, wherein predicting, by the processor, that the set of potential annoyance data is an actual annoyance is performed using machine learning.

3. The computer-implemented method of claim 2, wherein training data for the machine learning includes an input and output pair where the input is the first sound waveform segment and the output is the potential annoyance label.

4. The computer-implemented method of claim 2, wherein machine learning is repeated periodically.

5. The computer-implemented method of claim 1 further comprising collecting, by the processor, a video input feed of the user and using the video input feed when detecting and labeling a potential annoyance.

6. The computer implemented method of claim 1, wherein detecting and labeling as a potential annoyance, by the processor, the set of potential annoyance data from the collected physiological data and the sound waveform comprises finding patterns of abnormal changes in the physiological data.

7. The computer-implemented method of claim 1, wherein decomposing, by the processor, the sound waveform into a first sound waveform segment associated with the set of potential annoyance data and a second sound waveform segment not associated with the set of potential annoyance data comprises decomposing using a non-negative matrix factor 2-D deconvolution algorithm.

8. A system comprising:
a memory having computer readable instructions; and
one or more processors for executing the computer readable instructions, the computer readable instructions controlling the one or more processors to perform operations comprising:
collecting physiological data from a user in an environment and a sound waveform from the user's environment;
detecting and labeling as a potential annoyance a set of potential annoyance data based on the collected physiological data and the sound waveform;
decomposing the sound waveform into a first sound waveform segment associated with the set of potential annoyance data and a second sound waveform segment not associated with the set of potential annoyance data;
predicting that the set of potential annoyance data is an actual annoyance;
filtering and modifying the first sound waveform segment associated with the actual annoyance; and
providing the second sound waveform segment not associated with the actual annoyance to the user.

9. The system of claim 8, wherein predicting that the set of potential annoyance data is an actual annoyance is performed using machine learning.

10. The system of claim 9, wherein training data for the machine learning includes an input and output pair where the input is the first sound waveform segment and the output is the potential annoyance label.

11. The system of claim 10, wherein machine learning is repeated periodically.

12. The system of claim 8, further comprising collecting a video input feed of the user and using the video input feed when detecting and labeling a potential annoyance.

13. The system of claim 8, wherein detecting and labeling as a potential annoyance the set of potential annoyance data from the collected physiological data and the sound waveform comprises finding patterns of abnormal changes in the physiological data.

14. The system of claim 8, wherein decomposing the sound waveform into a first sound waveform segment associated with the set of potential annoyance data and a second sound waveform segment not associated with the set of potential annoyance data comprises decomposing using a non-negative matrix factor 2-D deconvolution algorithm.

15. A computer program product comprising one or more computer readable storage media having program instructions embodied therewith, the program instructions executable by a processor to cause the processor to perform operations comprising:
collecting physiological data from a user in an environment and a sound waveform from the user's environment;
detecting and labeling as a potential annoyance a set of potential annoyance data from the collected physiological data and the sound waveform;
decomposing the sound waveform into a first sound waveform segment associated with the set of potential annoyance data and a second sound waveform segment not associated with the set of potential annoyance data;
predicting that the set of potential annoyance data is an actual annoyance;
filtering and modifying the first sound waveform segment associated with the actual annoyance; and
providing the second sound waveform segment not associated with the actual annoyance to the user.

16. The computer program product of claim 15, wherein predicting that the set of potential annoyance data is an actual annoyance is performed using machine learning.

17. The computer program product of claim 16, wherein training data for the machine learning includes an input and output pair where the input is the first sound waveform segment and the output is the potential annoyance label.

18. The computer program product of claim 15, further comprising collecting a video input feed of the user and using the video input feed when detecting and labeling a potential annoyance.

19. The computer program product of claim 15, wherein detecting and labeling as a potential annoyance the set of potential annoyance data from the collected physiological data and the sound waveform comprises finding patterns of abnormal changes in the physiological data.

20. The computer program product of claim 15, wherein decomposing the sound waveform into a first sound waveform segment associated with the set of potential annoyance data and a second sound waveform segment not associated with the set of potential annoyance data comprises decomposing using a non-negative matrix factor 2-D deconvolution algorithm.

* * * * *